United States Patent [19]

Richter, Jr.

[11] Patent Number: 4,834,760
[45] Date of Patent: May 30, 1989

[54] BI-ARTICULATED PROSTHETIC TERMINAL DEVICE

[76] Inventor: Henry J. Richter, Jr., 827 Columbia St., Shreveport, La. 71104

[21] Appl. No.: 158,547

[22] Filed: Feb. 22, 1988

[51] Int. Cl.4 .............................................. A61F 2/54
[52] U.S. Cl. .................................... 623/65; 294/19.1
[58] Field of Search ....................... 623/57, 58, 61, 63, 623/64, 65; 294/19.1

[56] References Cited

U.S. PATENT DOCUMENTS

| 1,819,317 | 8/1931 | Baehr | 623/65 |
| 2,030,785 | 2/1936 | Dorrance | 623/65 |
| 4,089,072 | 5/1978 | Glabiszewski | 623/57 X |

FOREIGN PATENT DOCUMENTS

| 77996 | 1/1936 | Fed. Rep. of Germany | 623/57 |
| 112941 | 5/1921 | United Kingdom | 623/57 |
| 2109245 | 6/1983 | United Kingdom | 623/65 |

Primary Examiner—Richard J. Apley
Assistant Examiner—David J. Bender
Attorney, Agent, or Firm—John M. Harrison

[57] ABSTRACT

A bi-articulated prosthetic terminal device which is of the type having an upper proximal jaw and a lower proximal jaw pivotally connected at a proximal joint for handling relatively large, bulky and/or heavy items and a distal jaw assembly pivotally attached at a distal joint to the extending end of the upper proximal jaw and fitted with an upper distal jaw and a lower distal jaw. The lower distal jaw cooperates with the extending end of the lower proximal jaw at the distal joint to create the capability for handling small, thin and/or light items. In a first preferred embodiment of the invention, the distal jaw assembly is biased to close the lower distal jaw against the lower proximal jaw by means of a spring provided in the distal joint. In a second preferred embodiment, this bias is created by a rubber cushion situated between the upper distal jaw and the upper proximal jaw.

38 Claims, 1 Drawing Sheet

BI-ARTICULATED PROSTHETIC TERMINAL DEVICE

BACKGROUND OF THE INVENTION

FIELD OF THE INVENTION

This invention relates to prosthetic terminal devices and more particularly, to a bi-articulated prosthetic terminal device which is characterized by upper and lower proximal jaws that are pivotally joined at a proximal joint for handling large, bulky and/or heavy items and a distal jaw assembly pivotally attached to the upper proximal jaw at a distal joint and fitted with a lower distal jaw which cooperates with the lower proximal jaw, to handle small, light and/or thin items. In a preferred embodiment of the invention, a primary gripping tension or pinch force is provided in the upper proximal jaw and the lower proximal jaw by means of one or more rubber bands or O-rings which encircle the upper proximal jaw and low proximal jaw forwardly of the proximal joint, while a secondary gripping tension or pinch force is provided between the lower distal jaw and the lower proximal jaw by means of a spring located in the distal joint. In another preferred embodiment of the invention, the necessary tension is created in the distal joint by means of a rubber cushion which is seated between the upper distal jaw and the upper proximal jaw.

The bi-articulated prosthetic terminal device of this invention is characterized by the capability for handling both heavy, large and/or bulky items, as well as small, thin and/or light items. This capability is provided in the combination of a curved lower proximal jaw and a curved upper proximal jaw which are pivotally joined at a proximal joint and tensioned by one or more rubber bands or O-rings, in combination with a secondary, V-shaped distal jaw assembly which is pivotally attached to the upper proximal jaw. The bi-articulated prosthetic terminal device of this invention can be activated by conventional body-powered or externally-powered means and installation may be effected by standard connections such as the one-half-inch by twenty-inch threaded stud-to-wrist unit or by mounted bearing and friction ring-to-laminating ring connections which are well known to those skilled in the art. External power may be supplied by hydraulics and pneumatic systems, as well as electricity, in non-exclusive particular. Furthermore, due to the unique design of the bi-articulated prosthetic terminal device of this invention, the pinch force and the energy expenditure required for activation of this pinch force may be selected. Currently, the same energy is required to activate a conventional prosthetic terminal device, regardless of whether the object being acted on requires a greater or smaller pinch force for manipulation. Using the bi-articulated terminal device of this invention, very small, thin and/or light items may be grasped at the distal tip of the device by pivoting the distal joint assembly only, with the expenditure of much less energy than is necessary to activate the interior, primary proximal jaws. Accordingly, the bi-articulated prosthetic terminal device of this invention causes the "body powered" wearer less muscle and joint fatigue and also effects less battery drainage for the "externally powered" user.

Due to the nature of the control cable and harness elements of a terminal prosthetic device, the pinch force pressure in the device itself is directly proportional to sound side axilla pressure at the point of harness contact. Using the bi-articulated terminal device detailed herein, full operating pressure would be applied only when maximum pinch force is required, as described above, rather than indiscriminately, only for the purpose of opening the prosthetic terminal device. Furthermore, because of the progressive application of tension required to operate a conventional prosthetic terminal device through its full range of motion, either by external battery operation or by body power, an exceptionally smooth action is generated using the bi-articulated terminal device of this invention. This is due to the pre-loading effect of the light spring or the rubber cushion located in the distal jaw assembly, which pre-loading is necessary prior to operating the distal jaw assembly, where the heavier rubber band or O-ring which operates the upper and lower proximal jaws is stretched open. Not only is this arrangement considered to be easier on conventional gear trains and motors of externally-powered prosthetic terminal devices, but it also affords the body-powered wearer a smoother, less deliberate appearance when activating his or her bi-articulated prosthetic terminal device.

DESCRIPTION OF THE PRIOR ART

Prosthetic terminal devices have long been used to replace amputated limbs and to replace limbs which never developed due to congenital deformity. An early automatic artificial finger is detailed in U.S. Pat. No. 319,776, dated June 9, 1985, to Bayshore. The Bayshore finger includes multiple, articulated joints by a system of levers and gears and is mechanically operated by hand movements. U.S. Pat. No. 1,004,482, dated Sept. 26, 1911, to J. M. Shackelford, et al, details an "Artificial Hand" which is likewise controlled by a system of levers and gears and includes articulated finger joints attached to a hand member by movable linkages. A "Robot Controlled Limb" is detailed in U.S. Pat. No. 2,567,066, dated Sept. 4, 1951, to I. A. Goldman. The artificial limb is characterized by multiple articulated joints connected by pins and electrically operated by a system of wiring solenoids and switches connected to a battery pack. U.S. Pat. No. 4,094,016, dated June 13, 1978, to Gary Eroyan, details an "Artificial Hand and Forearm". The device includes an elongated housing open at the rear end to receive the stub of a human forearm and an adjacent upper arm adapted for securing thereto. A plate located within the housing pivotally mounts a series of finger assemblies, with the finger assemblies projecting from the housing. A thumb assembly is spaced from the finger assemblies and is pivotally mounted on the plate, with the thumb assembly projecting from the housing in opposed relationship with respect to the forefinger assembly. A camshaft is journalled on the plate and mounts a series of spaced cams, which respectfully register with the inner ends of the finger assemblies. The finger and thumb assemblies are operated by a reversible electric motor located within the housing and a switch is provided in cooperation with the motor, for moving the finger and thumb assemblies inwardly and outwardly at will by flexing muscles in the arm stub.

Artificial limbs which are not designed to resemble human hands and fingers are also well known in the art. U.S. Pat. No. 1,278,106, dated Sept. 10, 1918, to L. G. Caron, details an "Artificial Hand and Arm" which includes a "C"-shaped working member having a strap attached thereto for handing tools and implements, such as hoe and shovel handles and the like. U.S. Pat. No. 1,280,262, dated Oct. 1, 1981, to R. D. Maddox, details an artificial hand which is characterized by a curved primary hook portion provided with a slidably-adjustable, articulating mandible carried by the shank, or base of the hook portion for grasping objects and further including a locking mechanism for securing the sliding mandible in position on the hook shank. An "Artificial Hand Grip" is detailed in U.S. Pat. No. 1,289,400, dated Dec. 31, 1918, to Q. D. Corley. This patent details an adjustable claw-like terminal device having a fixed lever mandible and an upper mandible which is adjustable by means of a ratchet mechanism to change the access spacing between the mandibles. U.S. Pat. No. 1,423,296, dated July 18, 1922, to R. F. Armstrong, details an "Artificial Body Member" which incorporates a pair of curved, spaced-apart, fixed claw members and an adjustable claw member which may be slidably adjusted to nest inside the outside one of the fixed claw members at one extreme of movement and in close proximity to the opposite fixed claw member to retain smaller objects, in a second extreme sliding movement.

It is an object of this invention to provide a bi-articulated prosthetic terminal device which can be activated by body-powered or externally-powered means and may be installed by standard accepted techniques.

Another object of the invention is to provide a bi-articulated prosthetic terminal device which is designed to reduce the energy required to operate the device.

Yet another object of the invention is to provide a bi-articulated prosthetic terminal device which is designed for two-stage activation and use, wherein a first-operated distal joint assembly can be used to manipulate small, thin and/or light objects with minimum expenditure of energy and a second-operated proximal joint assembly can be activated to manipulate large, bulky and/or heavy objects.

Still another object of this invention is to provide a bi-articulated prosthetic terminal device which is characterized by a pair of primary proximal jaws pivotally joined at a proximal joint and tensioned by one or more rubber bands or O-rings to define proximal gripping means and a distal jaw assembly which is pivotally attached to the upper proximal jaw and cooperates with the lower proximal jaw to create a smaller distal gripping means.

Still another object of this invention is to provide a bi-articulated prosthetic terminal device which utilizes a pair of primary pivoting proximal jaws to handle large, heavy and/or bulky items and a cooperating set of distal jaws to handle small, light and/or thin objects, both of which jaw systems are activated by conventional body-powered or externally-powered operating means.

SUMMARY OF THE INVENTION

These and other objects of the invention are provided in a new and improved bi-articulated prosthetic terminal device which is characterized by upper and lower proximal jaws or mandibles that are pivotally joined at a proximal joint and tensioned by one or more rubber bands or O-rings to handle large, heavy and/or bulky items and a smaller distal joint assembly pivotally attached to the upper proximal jaw for handling small, light and/or thin objects between the lower distal jaw and the lower proximal jaw, which distal jaw assembly is tensioned by a spring or a rubber cushion.

BRIEF DESCRIPTION OF THE DRAWING

The invention will be better understood by reference to the accompanying drawing, wherein.

DESCRIPTION OF THE PREFERRED EMBODIMENTS

Figure 1:
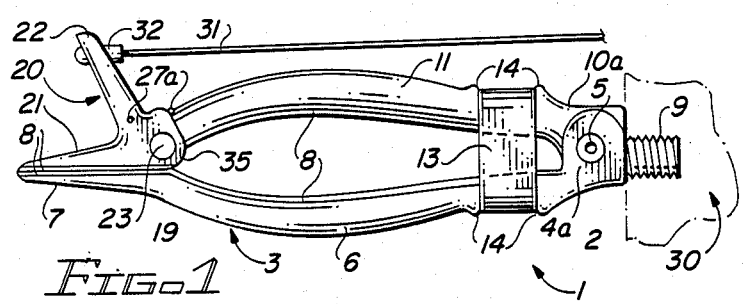
FIG. 1 is a side view of a first preferred embodiment of the bi-articulated prosthetic terminal device of this invention, with both the proximal jaws and the distal jaws positioned in closed configuration.
Figure 2:
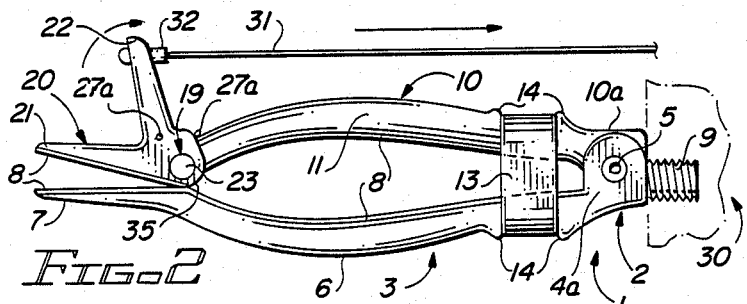
FIG. 2 is a side view of the bi-articulated prosthetic terminal device illustrated in FIG. 1, with the lower distal jaw opened with respect to the lower proximal jaw pursuant to user-generated tension applied to the operating cable.

Referring initially to FIGS. 1-4 of the drawings, a first preferred embodiment of the bi-articulated prosthetic terminal device is generally illustrated by reference numeral 1. The prosthetic terminal device 1 is characterized by a curved lower proximal jaw 3, which is joined to an oppositely-curved upper proximal jaw 10 at a proximal joint 2. The lower proximal jaw 3 is further characterized by a lower proximal jaw flange 4a provided in one end of the lower proximal jaw body 6, with a threaded base 9 extending rearwardly from fixed attachment to the jaw flange 4a. The base end of the upper proximal jaw body 11 is shaped to define an upper proximal jaw flange 10a, which pivotally engages the lower proximal jaw flange 4a and a proximal joint retainer 5 is fixedly attached to the lower proximal jaw flange 4a and threadibly cooperates with a companion proximal joint screw (not illustrated) to secure the base end of the upper proximal jaw body 11 in hinged attachment to the base end of the lower proximal jaw body 6. The lower proximal jaw body 6 extends forwardly of the lower proximal jaw flange 4a to define an extended, tapered lower proximal jaw tip 7 at the end thereof. A V-shaped distal jaw assembly 20 is pivotally attached at the distal jaw base 35 thereof, to the extending end of the upper proximal jaw body 11 by means of a distal joint pin 23. The distal jaw assembly 20 is constructed in a V-shaped configuration, in order to define a tapered lower distal jaw 21 which substantially matches the lower proximal jaw tip 7 extension of the lower proximal jaw body 6. The lower distal jaw 21 is normally closed on the lower proximal jaw tip 7, as illustrated in FIG. 1. An upper distal jaw 22 extends from the distal jaw base 35 of the distal jaw assembly 20 in angular relationship with respect to the companion lower distal jaw 21 and a cable mount notch 26 is provided in the extending end of the upper distal jaw 22, in order to receive a cable stay 32 for anchoring one end of an operating cable 31 to the upper distal jaw 22 of the distal jaw assembly 20. The cable 31 extends above the bi-articulated prosthetic terminal device 1 to a conventional arm-actuated linkage (not illustrated) for operating the bi-articulated prosthetic terminal deviced 1 by alternately tensioning the cable 31. The threaded base 9 is threaded into an arm cuff 30, illustrated in phantom, according to the knowledge of those skilled in the art, for mounting the bi-articulated prosthetic terminal device in conventional fashion on the stump of a limb. In a preferred embodiment of the invention, rubber or plastic gripping surfaces 8 are attached to or painted on the facing concave segments of the lower proximal jaw body 6 of the lower proximal jaw 3 and the upper proximal jaw body 11 of the upper proximal jaw 10, as illustrated. Additional gripping surfaces 8 may also be provided on the corresponding contact surfaces of the lower proximal jaw tip 7 and the lower distal jaw 21, respectively. A pair of jaw shoulders 14 are also provided in oppositely-disposed relationship in the lower proximal jaw body 6 and the upper proximal jaw body 11, in order to receive one or more rubber bands 13 for tensioning the lower proximal jaw 3 and the upper proximal jaw 10 in closed relationship, as illustrated in FIGS. 1 and 2. In another preferred embodiment of the invention, and referring specifically to FIG. 4, a distal joint spring 27 is utilized to tension the distal jaw assembly 20 in closed configuration, such that the lower distal jaw 21 is normally closed against the lower proximal jaw tip 7, as illustrated in FIG. 1. The distal joint spring 27 is further characterized by oppositely-disposed, projecting spring legs 27a, one of which spring legs 27a is disposed in the leg seat 33, provided in the distal jaw base 35 of the upper distal jaw 22, and the other spring leg 27a is positioned in the hinge seat 34, located at the juncture between the upper proximal jaw body 11 and the distal jaw base 35 of the distal jaw assembly 20, as further illustrated in FIGS. 1-4.

Figure 3:
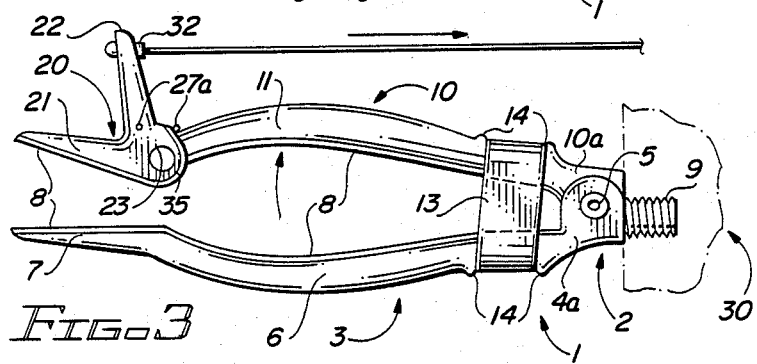
FIG. 3 is a side view of the bi-articulated prosthetic terminal device illustrated in FIGS. 1 and 2, with both the proximal jaws and the distal and lower proximal jaw opened by operation of the cable.

Referring now to FIGS. 1-3, when moderate tension is applied to the cable 31 by muscle or electrical operation of the bi-articulated prosthetic terminal device 1 according to the knowledge of those skilled in the art, this tension first causes the distal jaw assembly 20 to rotate on the distal jaw pin 23 and separate the lower distal jaw 21 from the underlying lower proximal jaw tip 7, as illustrated in FIG. 2. This manuever facilitates engagement of the optional gripping surfaces 8 provided in the facing contact surfaces of the lower distal jaw 21 and the companion lower proximal jaw tip 7 with a small or thin object such as a paper clip, sheet of paper, button or the like, (not illustrated) and subsequent release of tension in the cable 31 facilitates gripping this object between the lower distal jaw 21 and the lower proximal jaw tip 7 by operation of the tension in the distal jaw spring 27. When it is desired to grasp a larger or bulky object such as a pipe, board or the like, additional tension is then applied to the cable 31. Response to this increase in tension, the distal jaw assembly 20 pivots to a maximum open configuration with respect to the lower proximal jaw tip 7 and the upper proximal jaw body 11 then opens with respect to the lower proximal jaw body 6 against the tension or bias in the rubber band 13, by operation of the proximal joint 2. Accordingly, the upper proximal jaw 10 and the lower proximal jaw 3 are thus opened to a desired extent against the tension in the rubber band 13 as illustrated in FIG. 3, to grip the desired object between the respective gripping surfaces 8 provided in the lower proximal jaw body 6 and the upper proximal jaw body 11. Release of tension in the cable 31 allows the upper proximal jaw body 11 and the lower proximal jaw 3 to close on the object and grip the object between the lower proximal jaw body 6 and the upper proximal jaw body 11. Release of both the small object from its position between the lower distal jaw 21 and the lower proximal jaw tip 7 and the larger object from engagement between the upper proximal jaw body 11 and the lower proximal jaw body 6 is effected by reversing the procedure outlined above and reapplying tension in the cable 31.

Figure 4:
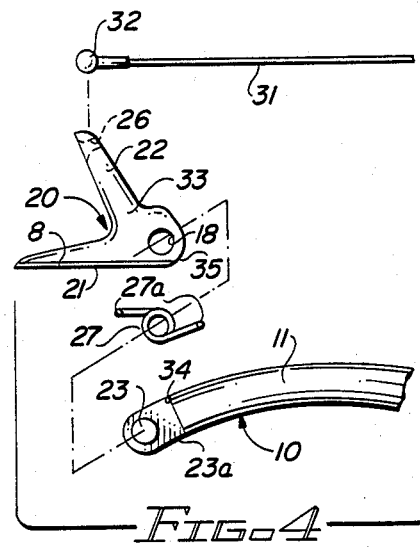
FIG. 4 is an exploded view of a first preferred distal jaw assembly.

Referring now to FIG. 4 of the drawing in a most preferred embodiment of the invention, the distal jaw assembly 20 is pivotally attached to the extending end of the upper proximal jaw body 11 of the upper proximal jaw 10 by means of a distal joint pin 23. The distal joint pin 23 is fixedly attached to, or formed integrally with the upper proximal jaw flange 10a at the piston seat 23a and receives the distal jaw assembly 20 by means of a hinged pin aperture 18 provided therein. Accordingly, when the distal jaw assembly 20 is seated on the distal joint pin 23 by registration of the distal joint pin 23 with the hinge pin aperture 18, the distal jaw assembly 20 is pivotally secured to the extending end of the upper proximal jaw body 11. Seating of the two projecting spring legs 27a of the distal joint spring 27 tightly in the leg seat 33 and the hinge seat 34, respectively, of the distal jaw base 35 of the distal jaw assembly 20 biases the lower distal jaw 21 in engagement with the underlying low proximal jaw tip 7, as heretofore described. The distal joint spring 27 further serves to maintain the distal joint assembly 20 on the distal joint pin 23 as the distal jaw assembly 20 pivots responsive to selective application and release of tension in the cable 31.

Figure 5:
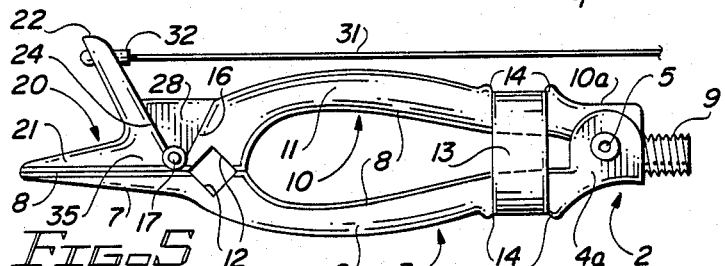
FIG. 5 is a side view of an alternative embodiment of the bi-articulated prosthetic terminal device of this invention.
Figure 8:
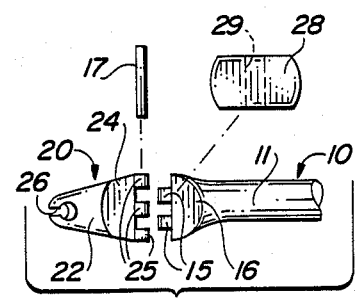
FIG. 8 is an exploded view of a preferred embodiment of the distal jaw assembly illustrated in FIGS. 5-7.
Figure 6:
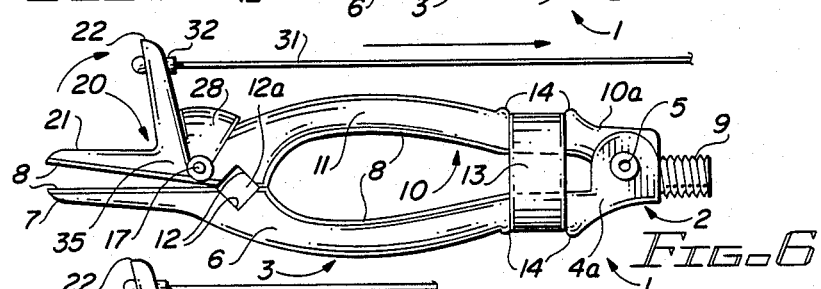
FIG. 6 is a side view of the bi-articulated prosthetic terminal device illustrated in FIG. 5, with the lower distal jaw opened with respect to the lower proximal jaw by user-manipulation of the operating cable.
Figure 9:
FIG. 9 is a side view of a preferred rubber cushion used to tension the distal jaw assembly illustrated in FIGS. 5-8 in closed configuration.
Figure 7:
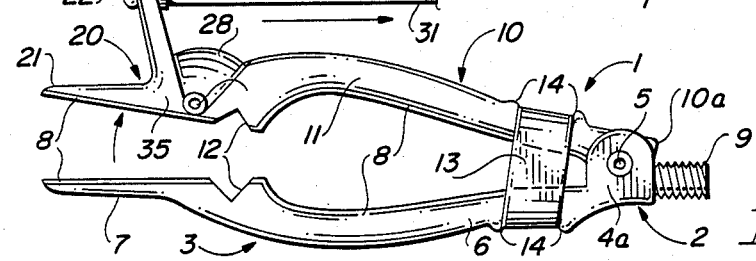
FIG. 7 is a side view of the bi-articulated prosthetic terminal device illustrated in FIG. 6, with both the proximal jaws and the lower distal jaw and the companion lower proximal jaw open pursuant to additional tension applied to the cable system.

Referring now to FIGS. 5-9 of the drawing in another preferred embodiment of the invention, the bi-articulated prosthetic terminal device 1 is characterized by a rubber cushion 28 disposed between the upper proximal jaw body 11 and the distal jaw base 35 of the distal jaw assembly 20. As further illustrated in FIGS. 8 and 9, the generally triangular-shaped rubber cushion 28 is characterized by a cushion notch 29 provided in an apex thereof, which cushion notch 29 engages a hinge pin 17 that serves to facilitate pivoting of the distal jaw assembly 20 on the extending end of the upper proximal jaw body 11 of the upper proximal jaw 10. Referring again to FIGS. 1-4 of the drawing, it will be appreciated that the distal jaw base 35 of the distal joint assembly 20 can be pivotally mounted on the upper proximal jaw body 11 in both the FIGS. 1-4 and FIGS. 5-9 embodiments of the invention using either the distal joint pin 23 or the hinge pin 17, as desired. In the FIGS. 5-9 embodiment of the invention, the extending end of the upper proximal jaw body 11 is provided with a shaped upper proximal jaw seat 16 for receiving one side of the rubber cushion 28, while the distal jaw base 35 of the upper distal jaw 22 is fitted with a similar upper distal jaw seat 24 for receiving the opposite side of the rubber cushion 28, as illustrated in FIGS. 5-7. In yet another preferred embodiment of the invention, three upper proximal jaw hinge retainers 25 extend in spaced relationship from the distal jaw base 35 at the base of the upper distal jaw seat 24, in order to receive corresponding upper proximal jaw hinge retainers 15, secured to the upper proximal jaw body 11 at the base of the corresponding upper proximal jaw seat 16. Accordingly, when the upper proximal jaw hinge retainers 15 are fitted into the spaces between the corresponding upper distal jaw hinge retainers 25, the hinge pin 17 is inserted through the registering openings provided therein and the distal jaw assembly 20 and the upper distal jaw 22 are pivotally attached to the extending end of the upper proximal jaw body 11. Accordingly, when a rubber cushion 28 of desired resiliency is inserted in the upper distal jaw seat 24 and the companion upper proximal jaw seat 16, the rubber cushion 28 serves to bias the lower distal jaw 21 against the underlying lower proximal jaw tip 7 in the same manner as the distal joint spring 27 illustrated in FIGS. 1-4 of the drawing. In yet another preferred embodiment of the invention, a pair of opposed jaw notches 12 are provided in oppositely-disposed relationship in the upper proximal jaw body 11 and the lower proximal jaw body 6, in order to facilitate more positive handling and manipulation of round and cylindrical items such as bearings, pipe, dowel rods and like items which are difficult to grip in other areas of the bi-articulated terminal prosthetic device 1. Otherwise, the bi-articulated prosthetic terminal device 1 illustrated in FIGS. 5-9 may be constructed substantially in the same manner as the bi-articulated prosthetic terminal device 1 illustrated in FIGS. 1-4. Accordingly, the bi-articulated prosthetic terminal device 1 illustrated in FIG. 5-9 is operated in the same manner as that illustrated in FIGS. 1-4, with the opening and closing of the distal jaw assembly 20 and the upper proximal jaw 10 with respect to the lower proximal jaw 3, respectively, controlled by the successive application and release of tension in the cable 31. This operation is illustrated with successively greater tension applied to the cable 31 in sequence, in FIGS. 5-7 of the drawing.

It will be recognized and understood by those skilled in the art that the tension applied to the cable 31 which is necessary to pivot the distal jaw assembly 20 on the upper proximal jaw body 11 and thereby open the lower distal jaw 21 with respect to the lower proximal jaw tip 7, will depend upon the tension in the distal joint spring 27 in the first embodiment of the invention and the resiliency of the rubber cushion 28 in the second embodiment of the invention. Accordingly, it is understood that separate distal joint springs 27 having a desired tension and bias profile, as well as various rubber cushions 28 having a different desired resiliency may be used, in order to vary the tension required to operate the distal jaw assembly 20. Furthermore, operation of the upper proximal jaw 10 with respect to the lower proximal jaw 3 is effected at a selected tension applied to the cable 31, by choosing a desired number of rubber bands 13 of desired resiliency and bias, in order to select the gripping force of the proximal joint 2.

The bi-articulated prosthetic terminal device of this invention offers a convenient and flexible means for gripping small, thin and/or light objects which might not otherwise be possible using only the articulation provided in the upper proximal jaw 10 and the lower proximal jaw 3. Furthermore, referring again to the drawing, since the distal jaw assembly 20 is pivotable downwardly farther than its normally engaging position against the lower proximal jaw tip 7, when a large object is located in the access space between the upper proximal jaw 10 and the lower proximal jaw 3, relaxation of the tension in the cable 31 facilitates extreme pivoting of the distal jaw assembly 20 on the distal joint pin 23 or the hinge pin 17, such that the lower distal jaw 21 may still touch the lower proximal jaw tip 7 to facilitate engagement and retention of smaller items therebetween. The bi-articulated prosthetic terminal device 1 can therefore be used to concurrently carry one or more items of varying size, weight and/or bulk, using both the distal jaw assembly 20 and the cooperating lower proximal jaw 3 and upper proximal jaw 10.

The bi-articulated prosthetic terminal device 1 of this invention may be manufactured or corrosion-proof, durable materials such as stainless steel and aluminum alloy, in non-exclusive particular, as well as injection-molded plastic materials, according to the knowledge of those skilled in the art. Furthermore, the interior opposed surfaces such as the gripping surfaces 8 located on the facing concave sides of the lower proximal jaw 3 and the upper proximal jaw 10 may be coated with rubber, plastic or other slip-resistant material, further according to the knowledge of those skilled in the art. Alternatively, this gripping surface may be serrated, knurled or otherwise textured, in order to facilitate positive gripping, as desired. Similarly, the contact surfaces in the lower distal jaw 21 and the lower proximal jaw tip 7 may be provided with a plastic or rubber gripping surface 8 or with textured or knurled surfaces, further according to the knowledge of those skilled in the art.

It will be further understood by those skilled in the art that the bi-articulated prosthetic terminal device of this invention, in both embodiments thereof, is characterized by two separate grasping areas which may be discriminately activated by means of a single conventional control system. Accordingly, two independent pinch forces of desired magnitude may be separately selected and maintained by means of this control system. Since the tension required to operate the distal jaw assembly 20 and facilitate carrying of small, light and/or thin items between the lower distal jaw 21 and the cooperating lower proximal jaw tip 7 is much reduced when compared to conventional threshold tension normally required in conventional terminal devices, the distal jaw assembly 20 may be operated with less power requirements, either in terms of external battery power or muscle energy. Furthermore, the bi-articulated prosthetic terminal device of this invention can be utilized by people of all ages and in all circumstances of handicap, with a high degree of accuracy and convenience.

While the preferred embodiments of the invention have been described above, it will be recognized and understood that various modifications may be made therein and the appended claims are intended to cover all such modifications which may fall within the spirit and scope of the invention.

Having described my invention with the particularity set forth above, what is claimed is:

1. A bi-articulated prosthetic terminal device for mounting on the stump of a limb comprising a lower proximal jaw; an upper proximal jaw pivotally carried by said lower proximal jaw; proximal jaw bias means engaging said lower proximal jaw and said upper proximal jaw for normally biasing said upper proximal jaw in close proximity to said lower proximal jaw; distal jaw means pivotally carried by said upper proximal jaw at a point along said upper proximal jaw apart from where said lower proximal jaw apart from where said lower proximal jaw pivotally carries said upper proximal jaw, said distal jaw means adapted to contact said lower proximal jaw when said distal jaw means is in closed configuration; distal jaw bias means provided in said distal jaw means for normally biasing said distal jaw means in said closed configuration; and operating means engaging said distal jaw means for selectively opening and closing said distal jaw means with respect to said lower proximal jaw and said upper proximal jaw with respect to said lower proximal jaw, respectively, whereby said distal jaw means is pivoted from contact with said lower proximal jaw against the bias of said distal jaw bias means into open configuration responsive to a first predetermined tension applied to said operating means and said upper proximal jaw is pivoted from said close proximity to said lower proximal jaw against the bias of said proximal jaw bias means into open configuration responsive to a second predetermined tension applied to said operating means wherein said first and second predetermined tensions are different.

2. The bi-articulated prosthetic terminal device of claim 1 wherein said proximal jaw bias means further comprises a rubber band.

3. The bi-articulated prosthetic terminal device of claim 1 wherein said proximal jaw bias means further comprises a resilient O-ring.

4. The bi-articulated prosthetic terminal device of claim 1 further comprising a lower proximal jaw flange projecting from one end of said lower proximal jaw, an upper proximal jaw flange projecting from a corresponding end of said upper proximal jaw, said upper proximal jaw flange engaging said lower proximal jaw flange, and fastening means connecting said upper proximal jaw flange and said lower proximal jaw flange to define a proximal joint, whereby said upper proximal jaw is pivotally attached to said lower proximal jaw at said proximal joint responsive to activation of said operating means.

5. The bi-articulated prosthetic terminal device of claim 4 wherein said proximal jaw bias means further comprises a rubber band engaging said upper proximal jaw and said lower proximal jaw adjacent to said proximal joint.

6. The bi-articulated prosthetic terminal device of claim 4 wherein said proximal jaw bias means further comprises a resilient O-ring engaging said upper proximal jaw and said lower proximal jaw adjacent to said proximal joint.

7. The bi-articulated prosthetic terminal device of claim 4 wherein said upper proximal jaw and said lower proximal jaw are curved to define an access space therebetween.

8. The bi-articulated prosthetic terminal device of claim 7 wherein said proximal jaw bias means further comprises a rubber band engaging said upper proximal jaw and said lower proximal jaw adjacent to said proximal joint.

9. The bi-articulated prosthetic terminal device of claim 7 wherein said proximal jaw bias means further comprises a resilient O-ring engaging said upper proximal jaw and said lower proximal jaw adjacent to said proximal joint.

10. The bi-articulated prosthetic terminal device of claim 4 further comprising a threaded nipple fixedly secured to a selected one of said upper proximal jaw flange and said lower proximal jaw flange, for securing said bi-articulated prosthetic terminal device to the stump of the limb.

11. The bi-articulated prosthetic terminal device of claim 10 wherein said upper proximal jaw and said lower proximal jaw are curved to define an access space therebetween.

12. The bi-articulated prosthetic terminal device of claim 11 wherein said proximal jaw bias means further comprises a rubber band engaging said upper proximal jaw and said lower proximal jaw adjacent to said proximal joint.

13. The bi-articulated prosthetic terminal device of claim 11 wherein said proximal jaw bias means further comprises a resilient O-ring engaging said upper proximal jaw and said lower proximal jaw adjacent to said proximal joint.

14. The bi-articulated prosthetic terminal device of claim 1 wherein said distal jaw means further comprises a lower distal jaw normally biased in contact with said lower proximal jaw by said distal jaw bias means and an upper distal jaw extending from said lower distal jaw in angular relationship, said upper distal jaw adapted to receive and anchor said operating means.

15. The bi-articulated prosthetic terminal device of claim 14 further comprising a lower proximal jaw flange projecting from one end of said lower proximal jaw, an upper proximal jaw flange projecting from a corresponding end of said upper proximal jaw, said upper proximal jaw flange engaging said lower proximal jaw flange, and fastening means connecting said upper proximal jaw flange and said lower proximal jaw flange to define a proximal joint, whereby said upper proximal jaw is pivotally attached to said lower proximal jaw at said proximal joint responsive to activation of said operating means.

16. The bi-articulated prosthetic terminal device of claim 15 wherein said upper proximal jaw and said lower proximal jaw are curved to define an access space therebetween.

17. The bi-articulated prosthetic terminal device of claim 15 further comprising a threaded nipple fixedly secured to a selected one of said upper proximal jaw flange and said lower proximal jaw flange, for securing said bi-articulated prosthetic terminal device to the stump of the limb.

18. The bi-articulated prosthetic terminal device of claim 17 wherein said proximal jaw bias means further comprises a rubber band engaging said upper proximal jaw and said lower proximal jaw adjacent to said proximal joint.

19. The bi-articulated prosthetic terminal device of claim 17 wherein said proximal jaw bias means further comprises a resilient O-ring engaging said upper proximal jaw and said lower proximal jaw adjacent to said proximal joint.

20. The bi-articulated prosthetic terminal device of claim 17 wherein said distal jaw bias means further comprises a spring having a selected spring tension, said spring also having one end provided in engagement with said distal jaw means and the opposite end of said spring engaging said upper proximal jaw and said operating means further comprises a cable having one end attached to said upper distal jaw and the other end adapted to be carried by the stump.

21. The bi-articulated prosthetic terminal device of claim 17 wherein said distal jaw bias means further comprises a resilient cushion having a selected elasticity disposed between said upper distal jaw and said upper proximal jaw, and said operating means further comprises a cable having one end attached to said upper distal jaw and the other end carried by the stump.

22. The bi-articulated prosthetic terminal device of claim 14 wherein said distal jaw bias means further comprises a resilient cushion having a selected elasticity disposed between said upper distal jaw and said upper proximal jaw and said operating means further comprises a cable having one end attached to said upper distal jaw and the other end adapted to be carried by the stump.

23. The bi-articulated prosthetic terminal device of claim 1 wherein said distal jaw bias means further comprises a spring having a selected spring tension, said spring also having one end provided in engagement with said distal jaw means and the opposite end of said spring engaging said upper proximal jaw.

24. A bi-articulated prosthetic terminal device for mounting on the stump of a limb comprising a lower proximal jaw; an upper proximal jaw pivotally carried by said lower proximal jaw; proximal jaw bias means engaging said lower proximal jaw and said upper proximal jaw for normally biasing said upper proximal jaw in closed configuration against said lower proximal jaw; a distal jaw assembly pivotally carried by said upper proximal jaw at a point along said upper proximal jaw apart from where said lower proximal jaw pivotally carries said upper proximal jaw, said distal jaw assembly having a lower distal jaw adapted to contact said lower proximal jaw when said lower distal jaw is in said closed configuration and an upper distal jaw disposed in angular relationship with respect to said lower distal jaw; distal jaw bias means provided in said distal jaw assembly for normally biasing said lower distal jaw against said lower proximal jaw; and operating means engaging said upper distal jaw for selectively opening and closing said lower distal jaw with respect to said lower proximal jaw and said upper proximal jaw with respect to said lower proximal jaw, respectively, whereby said lower distal jaw is pivoted from contact with said lower proximal jaw against the bias of said distal jaw bias means into open configuration responsive to a first predetermined tension applied to said operating means and said upper proximal jaw is pivoted from said closed configuration against said lower proximal jaw against the bias of said proximal jaw bias means into open configuration responsive to a second predetermined tension applied to said operating means wherein said first and second predetermined tensions are different.

25. The bi-articulated prosthetic terminal device of claim 24 wherein:
(a) said distal jaw bias means further comprises a spring having a selected spring tension, said spring also having one end provided in engagement with said upper distal jaw and the opposite end of said spring engaging said upper proximal jaw; and
(b) said proximal jaw bias means further comprises a rubber band engaging said upper proximal jaw and said lower proximal jaw adjacent to said proximal joint.

26. The bi-articulated prosthetic terminal device of claim 25 further comprising a lower proximal jaw flange projecting from one end of said lower proximal jaw, an upper proximal jaw flange projecting from a corresponding end of said upper proximal jaw, said upper proximal jaw flange pivotally engaging said lower proximal jaw flange, and fastening means connecting said upper proximal jaw flange and said lower proximal jaw flange to define a proximal joint, whereby said upper proximal jaw is pivotally attached to said lower proximal jaw at said proximal joint responsive to activation of said operating means.

27. The bi-articulated prosthetic terminal device of claim 26 further comprising a threaded nipple fixedly secured to a selected one of said upper proximal jaw flange and said lower proximal jaw flange, for securing said bi-articulated prosthetic terminal device to the stump of the limb.

28. The bi-articulated prosthetic terminal device of claim 27 wherein:
(a) said distal jaw bias means further comprises a spring having a selected spring tension, said spring also having one end provided in engagement with said upper distal jaw and the opposite end of said spring engaging said upper proximal jaw;
(b) said proximal jaw bias means further comprises a rubber band engaging said upper proximal jaw and said lower proximal jaw adjacent to said proximal joint; and
(c) said operating means further comprises a cable having one end attached to said upper distal jaw and the other end adapted to be carried by the stump.

29. The bi-articulated prosthetic terminal device of claim 27 wherein:
(a) said distal jaw bias means further comprises a resilient cushion having a selected elasticity disposed between said upper distal jaw and said upper proximal jaw;
(b) said proximal jaw bias means further comprises a rubber band engaging said upper proximal jaw and said lower proximal jaw adjacent to said proximal joint; and
(c) said operating means further comprises a cable having one end attached to said upper distal jaw and the other end adapted to be carried by the stump.

30. The bi-articulated prosthetic terminal device of claim 24 wherein:
(a) said distal jaw bias means further comprises a resilient cushion having a selected elasticity disposed between said upper distal jaw and said upper proximal jaw; and
(b) said proximal jaw bias means further comprises a rubber band engaging said upper proximal jaw and said lower proximal jaw adjacent to said proximal joint.

31. The bi-articulated prosthetic terminal device of claim 24 wherein:
(a) said distal jaw bias means further comprises a spring having a selected spring tension, said spring also having one end provided in engagement with said upper distal jaw and the opposite end of said spring engaging said upper proximal jaw; and
(b) said proximal jaw bias means further comprises a resilient O-ring engaging said upper proximal jaw and said lower proximal jaw adjacent to said proximal joint.

32. A bi-articulated prosthetic terminal device for mounting on the stump of an arm comprising an elongated, curved lower proximal jaw; an elongated, curved upper proximal jaw having one end pivotally carried by a corresponding end of said lower proximal jaw; resilient proximal jaw bias means engaging said upper proximal jaw and said lower proximal jaw for normally biasing the opposite end of said upper proximal jaw into contact with said lower proximal jaw; a distal jaw base pivotally attached to the opposite end of said upper proximal jaw; a lower distal jaw extending from said distal jaw base; an upper distal jaw projecting from said distal jaw base in angular relationship with respect to said lower distal jaw; distal jaw bias means connecting said upper proximal jaw and said upper distal jaw for normally biasing said lower distal jaw against said lower proximal jaw; and an operating cable having one end attached to said upper distal jaw and the other end of said operating cable is adapted for communicating with said stump, whereby said lower distal jaw is pivoted from contact with said lower proximal jaw against the bias of said distal jaw bias means responsive to a first predetermined tension applied to said operating cable and said upper proximal jaw is pivoted from contact with said lower proximal jaw against the bias of said proximal jaw bias means responsive to a second predetermined tension applied to said operating cable wherein said first and second predetermined tensions are different.

33. The bi-articulated prosthetic terminal device of claim 32 wherein:
  (a) said distal jaw bias means further comprises a spring having a selected spring tension, said spring also having one end provided in engagement with said upper distal jaw and the opposite end of said spring engaging said upper proximal jaw; and
  (b) said proximal jaw bias means further comprises a rubber band engaging said upper proximal jaw and said lower proximal jaw adjacent to said proximal joint.

34. The bi-articulated prosthetic terminal device of claim 32 wherein:
  (a) said distal jaw bias means further comprises a resilient cushion having a selected elasticity disposed between said upper distal jaw and said upper proximal jaw; and
  (b) said proximal jaw bias means further comprises a rubber band engaging said upper proximal jaw and said lower proximal jaw adjacent to said proximal joint.

35. The bi-articulated prosthetic terminal device of claim 32 further comprising a first notch provided in said upper proximal jaw and a second notch provided in said lower proximal jaw, said first notch and said second notch joining to define an auxiliary gripping space when said upper proximal jaw is closed on said lower proximal jaw.

36. The bi-articulated prosthetic terminal device of claim 35 further comprising a lower proximal jaw flange projecting from one end of said lower proximal jaw, an upper proximal jaw flange projecting from a corresponding end of said upper proximal jaw, said upper proximal jaw flange pivotally engaging said lower proximal jaw flange, and fastening means connecting said upper proximal jaw flange and said lower proximal jaw flange to define a proximal joint, whereby said upper proximal jaw is pivotally attached to said lower proximal jaw at said proximal joint responsive to activation of said operating cable.

37. The bi-articulated prosthetic terminal device of claim 36 wherein:
  (a) said distal jaw bias means further comprises a spring having a selected spring tension, said spring also having one end provided in engagement with said upper distal jaw and the opposite end of said spring engaging said upper proximal jaw; and
  (b) said proximal jaw bias means further comprises a rubber band engaging said upper proximal jaw and said lower proximal jaw adjacent to said proximal joint.

38. The bi-articulated prosthetic terminal device of claim 36 wherein:
  (a) said distal jaw bias means further comprises a resilient cushion having a selected elasticity disposed between said upper distal jaw and said upper proximal jaw; and
  (b) said proximal jaw bias means further comprises a rubber band engaging said upper proximal jaw and said lower proximal jaw adjacent to said proximal joint.

* * * * *